US012805811B2

(12) United States Patent
Wu et al.

(10) Patent No.: US 12,805,811 B2
(45) Date of Patent: Nov. 24, 2026

(54) PATIENT MONITORING DEVICE AND ALARM METHOD FOR PATIENT MONITORING

(71) Applicants: SHENZHEN MINDRAY BIO-MEDICAL ELECTRONICS CO., LTD., Shenzhen (CN); XI'AN SHEN MINDRAY MEDICAL ELECTRONICS TECHNOLOGY RESEARCH INSTITUTE CO., LTD., Xian (CN)

(72) Inventors: Xuelei Wu, Shenzhen (CN); Jian Cheng, Xian (CN); Kun Zhao, Xian (CN); Kexin Hao, Shenzhen (CN); Shuaijun Liu, Shenzhen (CN)

(73) Assignees: SHENZHEN MINDRAY BIO-MEDICAL ELECTRONICS CO., LTD., Shenzhen (CN); XI'AN SHEN MINDRAY MEDICAL ELECTRONICS RESEARCH INSTITUTE CO., LTD., Xi'an (CN)

( * ) Notice: Subject to any disclaimer, the term of this patent is extended or adjusted under 35 U.S.C. 154(b) by 177 days.

(21) Appl. No.: 18/761,068

(22) Filed: Jul. 1, 2024

(65) Prior Publication Data

US 2025/0120658 A1 Apr. 17, 2025

Related U.S. Application Data

(63) Continuation of application No. PCT/CN2023/070057, filed on Jan. 3, 2023.

(30) Foreign Application Priority Data

Dec. 31, 2021 (CN) ........................ 202111676236.3

(51) Int. Cl.
*G08B 23/00* (2006.01)
*A61B 5/00* (2006.01)
(Continued)

(52) U.S. Cl.
CPC ............ *A61B 5/746* (2013.01); *A61B 5/0205* (2013.01); *A61B 5/743* (2013.01); *A61B 5/021* (2013.01);
(Continued)

(58) Field of Classification Search
CPC ....... A61B 5/746; A61B 5/0205; A61B 5/743; A61B 5/021; A61B 5/08; A61B 5/14542;
(Continued)

(56) References Cited

U.S. PATENT DOCUMENTS 8,665,096 B2 3/2014 Rantala et al.
8,840,549 B2 * 9/2014 Al-Ali ................ A61B 5/14532 600/301
(Continued)

FOREIGN PATENT DOCUMENTS

CN 102048543 A 5/2011
CN 102663873 A 9/2012
(Continued)

OTHER PUBLICATIONS

PCT International Search Report and the Written Opinion mailed Mar. 31, 2023, issued in related International Application No. PCT/CN2023/070057, with partial English translation (12 pages).
(Continued)

*Primary Examiner* — Toan N Pham
(74) *Attorney, Agent, or Firm* — Sheppard Mullin Richter & Hampton LLP

(57) ABSTRACT

A patient monitoring device and method. The device comprises: a signal acquirer (10), used for acquiring a physiological parameter signal of at least one physiological
(Continued)

parameter of a patient; a processor (20), used for generating a first alarm when the physiological parameter signal of the at least one physiological parameter satisfies a first alarm rule; and a display (30), used for displaying first alarm information in a first alarm area in a first presentation manner, wherein the first alarm information is used for representing the first alarm; and the display (30) is further used for displaying the first alarm information in a second presentation manner when the physiological parameter signal of the at least one physiological parameter simultaneously satisfies the first alarm rule and a second alarm rule, wherein the second alarm rule is different from the first alarm rule, and the second presentation manner is an upgrade based on the first presentation manner, so as to remind a medical staff about the increase of pathological risk of the patient to intervene in time.

20 Claims, 4 Drawing Sheets

(51) Int. Cl.

| | |
|---|---|
| ***A61B 5/0205*** | (2006.01) |
| *A61B 5/021* | (2006.01) |
| *A61B 5/08* | (2006.01) |
| *A61B 5/145* | (2006.01) |
| *A61B 5/346* | (2021.01) |

(52) U.S. Cl.
CPC ............ *A61B 5/08* (2013.01); *A61B 5/14542* (2013.01); *A61B 5/346* (2021.01)

(58) Field of Classification Search
CPC ........... A61B 5/346; A61B 5/00; A61B 5/145; G08B 21/02; G08B 23/00
See application file for complete search history.

(56) References Cited

U.S. PATENT DOCUMENTS

| | | | | |
|---|---|---|---|---|
| 9,265,429 | B2 * | 2/2016 | St. Pierre | A61B 5/7475 |
| 9,398,884 | B2 | 7/2016 | Tanishima et al. | |
| 9,943,269 | B2 * | 4/2018 | Muhsin | A61B 5/02055 |
| 11,006,904 | B2 * | 5/2021 | Murai | G08B 21/0446 |
| 2015/0257716 | A1 * | 9/2015 | Humphrys | A61B 5/02055 600/300 |
| 2016/0166148 | A1 | 6/2016 | Malkki | |
| 2019/0117070 | A1 | 4/2019 | Muhsin et al. | |
| 2019/0320988 | A1 | 10/2019 | Ahmed et al. | |

FOREIGN PATENT DOCUMENTS

| | | | |
|---|---|---|---|
| CN | 203417195 | U | 2/2014 |
| CN | 104116502 | A | 10/2014 |
| JP | 2019-061349 | A | 4/2019 |

OTHER PUBLICATIONS

PCT International Preliminary Report on Patentability mailed Jul. 11, 2024, issued in related International Application No. PCT/CN2023/070057, with English translation (12 pages).

* cited by examiner

PATIENT MONITORING DEVICE AND ALARM METHOD FOR PATIENT MONITORING

CROSS-REFERENCE TO RELATED APPLICATIONS

This application is a continuation application of International Patent Application No. PCT/CN2023/070057, filed on Jan. 3, 2023, which is based on and claims priority to and benefits of Chinese Patent Application No. 202111676236.3, filed on Dec. 31, 2021. The entire content of all of the above-referenced applications is incorporated herein by reference.

TECHNICAL FIELD

The disclosure relates to a technical field for a medical device, and more particularly to a patient monitoring device and an alarm method for patient monitoring.

BACKGROUND

Patient monitoring device has a function of detecting various physiological parameter signals of a patient, and can also send an alarm when the physiological parameter signals are abnormal, so that medical staff can manage the patient more conveniently. Conventional patient monitoring device only has a single alarm function based on a single physiological parameter. For example, when the patient monitoring device is provided with an alarm for exceeding a threshold of an SpO2 (blood oxygen saturation) parameter, and its alarm level is preset to be medium level. When the patient monitoring device detects that an SpO2 parameter value is lower than a lower threshold of the SpO2 parameter, an alarm character string of "SpO2 too-low" automatically pops up in an alarm area of the device with a yellow background. At the same time, a medium-level alarm sound and light are used to remind medical staff to pay attention to this single alarm generated based on the signal of blood oxygen saturation parameter. Similarly, when the patient monitoring device is a multi-parameter monitoring device, the patient monitoring device is usually also provided with single alarms based on other physiological parameters, such as an alarm for exceeding a threshold of an RR parameter based on a respiratory parameter, and its alarm level is preset to be medium level. When an RR parameter value detected is lower than a lower threshold of the RR parameter, an alarm character string of "RR too-low" will automatically pop up in the alarm area of the device with a yellow background. At the same time, the medium-level alarm sound and light are used to remind medical staff to pay attention to this single alarm generated based on the respiratory parameter signal. If the patient monitoring device detects that an SpO2 parameter value is lower than the lower threshold of the SpO2 parameter and an RR parameter value is lower than the lower threshold of the RR parameter at the same time, alarm characters "SpO2 too-low" and "RR too-low" are displayed alternately in the same alarm area with a yellow background, and a medium-level alarm sound and light are used to remind. This alarm mode causes medical staff to focus mainly on single alarm information, and they are prone to ignore or simply fail to notice two or more related alarms occurring simultaneously among so many alarm characters displayed alternately. These related and simultaneous alarms often represent a more serious physiological condition of the patient, or represent that the physiological condition of the patient is or is about to deteriorate. Although particularly experienced medical staff can determine from experience that the simultaneous occurrence of different single alarms may increase a pathological risk of the patient, overall, ignoring or failing to notice the existence of two or more alarms that indicate a more serious, or currently deteriorating or soon-to-be-deteriorating, physiological condition of the patient still affects timeliness of intervention of medical staff to the patient.

SUMMARY

This disclosure aims to provide a patient monitoring device and an alarm method for patient monitoring, which enables the patient monitoring device to provide more targeted alarm presentation, so as to help medical staff to implement an intervention for a patient in a timely manner.

An embodiment provides a patient monitoring device, including:

a signal acquiring apparatus, which is configured to acquire a physiological parameter signal of at least one physiological parameter for a patient;

a processor, which is configured to process the physiological parameter signal of the at least one physiological parameter, and generate a first alarm when determining that the physiological parameter signal of the at least one physiological parameter satisfies a first alarm rule; and a display, which is configured to display, in a first alarm area, first alarm information in a first presentation mode, wherein the first alarm information represents the first alarm;

wherein the processor is further configured to control the display to display the first alarm information in a second presentation mode, when determining that the physiological parameter signal of the at least one physiological parameter simultaneously satisfies the first alarm rule and a second alarm rule; wherein the second alarm rule is different from the first alarm rule, and the second presentation mode is an upgrade based on the first presentation mode.

In a preferable embodiment, the first presentation mode includes displaying the first alarm information in the first alarm area with a first background color;

the second presentation mode includes one mode of:

displaying the first alarm information in the first alarm area with a second background color, wherein the second background color has a stronger warning effect than the first background color;

enlarging the first alarm area, and displaying the first alarm information in the enlarged first alarm area;

displaying the first alarm information in the first alarm area with the first background color or a second background color, wherein the first background color or the second background color is flashed;

displaying the first alarm information in a second alarm area which is outside the first alarm area.

In a preferable embodiment, the second presentation mode includes simultaneously displaying second alarm information and the first alarm information in an associated combination mode;

wherein the second alarm information represents that the physiological parameter signal of the at least one physiological parameter satisfies the second alarm rule.

In a preferable embodiment, the second alarm information is in associated combination with the first alarm information through an associated character string.

In a preferable embodiment, the associated character string includes text, symbol(s), and/or mark(s).

In a preferable embodiment, the second alarm information and the first alarm information are simultaneously displayed in the associated combination mode in a second alarm area, wherein the second alarm area is independent from the first alarm area.

In a preferable embodiment, the second alarm information and the first alarm information are simultaneously displayed in the associated combination mode in the first alarm area.

In a preferable embodiment, the first alarm area and the second alarm area are arranged side by side, from up to down or from left to right.

In a preferable embodiment, a background color of the first alarm area has a stronger warning effect than a background color of the second alarm area.

In a preferable embodiment, the patient monitoring device further includes an audio outputting apparatus, wherein the second presentation mode includes: adding or enhancing, through the audio outputting apparatus, an alarm sound along with a presentation of the first alarm information.

In a preferable embodiment, the at least one physiological parameter includes a first physiological parameter, the physiological parameter signal includes a first physiological parameter signal; wherein the first alarm rule and the second alarm rule are both associated with the first physiological parameter.

In a preferable embodiment, the first alarm rule is an alarm rule for exceeding a threshold or an alarm rule for an event, which rules are associated with the first physiological parameter; the second alarm rule is that a duration of an alarm exceeds a preset time length, which alarm satisfies the first alarm rule.

In a preferable embodiment, the first physiological parameter includes a blood oxygen saturation parameter, an electrocardiogram parameter, a respiratory parameter, or a blood pressure parameter;

the first alarm rule includes that the first physiological parameter signal exceeds an alarm threshold.

In a preferable embodiment, the at least one physiological parameter includes a first physiological parameter and a second physiological parameter that is different from the first physiological parameter; the physiological parameter signal includes a first physiological parameter signal and a second physiological parameter signal; the first alarm rule is associated with the first physiological parameter, and the second alarm rule is associated with the second physiological parameter.

In a preferable embodiment, the first physiological parameter is a blood oxygen saturation parameter; the first alarm includes an alarm for extremely-low SpO2, an alarm for too-low SpO2, an alarm for extremely-low SpO2b, or an alarm for too-low SpO2b;

the second physiological parameter is a respiratory parameter, the second alarm rule is that a signal of said respiratory parameter satisfies a threshold for too-high respiratory rate, or a threshold for too-low respiratory rate.

In a preferable embodiment, the first physiological parameter is a blood pressure parameter, the first alarm rule includes an alarm rule for too-low arterial pressure;

the second physiological parameter is an electrocardiogram parameter; the second alarm rule includes at least one of: an alarm rule for too-low HR, an alarm rule for bradycardia, an alarm rule for tachycardia, an alarm rule for atrial fibrillation, an alarm rule for ventricular rhythm, an alarm rule for bigeminy ventricular premature contraction, an alarm rule for trigeminy premature ventricular contraction, an alarm rule for too-high ST, an alarm rule for too-low ST, an alarm rule for a single ΔST that exceeds a threshold, and an alarm rule for multiple ΔSTs that exceed threshold(s).

In a preferable embodiment, the processor is further configured to control the display to simultaneously present the first alarm information and second alarm information in an associated combination mode, when determining that the first physiological parameter satisfies the first alarm rule, and the second physiological parameter satisfies the second alarm rule;

the second alarm rule includes: the second physiological parameter satisfies an alarm rule for exceeding a threshold and/or an alarm rule for an event; and duration(s) exceed(s) preset time length(s), in which duration(s) the second physiological parameter satisfies the alarm rule for exceeding a threshold and/or the alarm rule for an event;

wherein the first alarm information represents that the first physiological parameter satisfies the first alarm rule, and the second alarm information represents that the second physiological parameter satisfies the second alarm rule.

In a preferable embodiment, the display further includes an alarm setting interface, wherein the first alarm rule and the second alarm rule are set through the alarm setting interface;

wherein the alarm setting interface includes a setting interface for combined alarm, wherein the setting interface for combined alarm is configured to display a first alarm setting and a second alarm setting in an associated combination mode, wherein the first alarm setting is configured to generate or display the first alarm rule, and the second alarm setting is configured to generate or display the second alarm rule.

In a preferable embodiment, the first alarm rule includes: an alarm rule for exceeding a threshold and/or an alarm rule for an event, which alarm rule(s) is(are) associated with a first physiological parameter;

the second alarm rule includes: an alarm rule for exceeding a threshold and/or an alarm rule for an event, which alarm rule(s) is(are) associated with a second physiological parameter, wherein the second physiological parameter is different from the first physiological parameter.

In a preferable embodiment, when at least one of the first alarm rule and the second alarm rule includes an alarm rule for exceeding a threshold;

the processor is further configured to, when receiving an instruction for adjusting a threshold, which instruction is for an alarm threshold of said alarm rule for exceeding a threshold, adjust the alarm threshold of said alarm rule for exceeding a threshold, to a threshold which is instructed by said instruction.

In a preferable embodiment, the setting interface for combined alarm further includes a delay setting option;

wherein the delay setting option is configured to indicate or set the first alarm information to be presented in the second presentation mode; when the physiological parameter signal simultaneously satisfies the first alarm rule and the second alarm rule, and a duration exceeds a first preset time length, in which duration the physiological parameter signal simultaneously satisfies the first alarm rule and the second alarm rule; or the delay setting option is configured to indicate or set the first alarm information to be presented in the second presentation mode, when the physiological parameter signal satisfies the first alarm rule, and a duration exceeds a second preset time length, in which duration the physiological parameter signal satisfies the first alarm rule.

In a preferable embodiment, when an instruction for adjusting a time length is inputted through the delay setting option, the processor is further configured to adjust the first preset time length or the second preset time length to a time length which is instructed by said instruction.

An embodiment provides a patient monitoring device, including:

a signal acquiring apparatus, which is configured to acquire a physiological parameter signal of at least one physiological parameter for a patient;

a processor, which is configured to generate a first alarm when the physiological parameter signal of the at least one physiological parameter satisfies a first alarm rule, and generate a second alarm when the physiological parameter signal of the at least one physiological parameter satisfies a second alarm rule; and a display, which is configured to display first alarm information and second alarm information; wherein the first alarm information represents the first alarm, and the second alarm information represents the second alarm;

wherein the display is further configured to output, in a combined alarm mode, the first alarm information and the second alarm information, when the physiological parameter signal of the at least one physiological parameter simultaneously satisfies the first alarm rule and the second alarm rule.

In a preferable embodiment, the combined alarm mode includes combining the first alarm information and the second alarm information through an associated character string and displaying the combination; wherein the associated character string represents that the second alarm accompanies with the first alarm.

In a preferable embodiment, the processor is further configured to analyse the physiological parameter signal according to a preset rule, so as to obtain a patient state of the patient; wherein the patient state includes one or more of an overall state, a physiological system state, an organ state, a physiological part state, and a tissue state; and the display is further configured to present, on a human body diagram, the patient state;

and present at least one item of alarm information in a combined alarm mode, which information is associated with the patient state.

In a preferable embodiment, the patient state is presented by marking the human body diagram;

wherein when the patient state includes the overall state, an entirety of the human body diagram is marked;

when the patient state includes one or more of the physiological system state, the organ state, the physiological part state, and the tissue state; one or more of a physiological system, an organ, a physiological part, and a tissue, which correspond(s) to said patient state, is(are) marked.

In a preferable embodiment, the human body diagram is marked via at least one of graph information, symbol information, color information, and text information, which information is displayed on or adjacent to the human body diagram, so as to present the patient state.

In a preferable embodiment, the patient state further includes one or more of: whether one or more of the overall state, the physiological system state, the organ state, the physiological part state, and the tissue state is(are) abnormal or not; an abnormality level; a criticality level; and a nursing level.

In a preferable embodiment, in order to present the alarm information in a combined alarm mode, the display is further configured to:

combine and display, an alarm for exceeding a threshold and/or an alarm for an event, which alarm(s) is(are) for at least one physiological parameter which is associated with the patient state, and duration(s) of the alarm for exceeding a threshold and/or the alarm for an event; and/or combine and display, alarms for exceeding a threshold, which alarms are for at least two physiological parameters which are associated with the patient state.

In a preferable embodiment, the processor is further configured to present, on the display, a trend graph of at least one physiological parameter signal in a preset time period; wherein the trend graph is configured to reflect an evolution of said at least one physiological parameter signal in the preset time period.

An embodiment provides an alarm method for patient monitoring, including:

acquiring a physiological parameter signal of at least one physiological parameter for a patient;

processing the physiological parameter signal of the at least one physiological parameter, and generating first alarm information which corresponds to a first alarm, when the physiological parameter signal of the at least one physiological parameter is determined to satisfy a first alarm rule;

processing the physiological parameter signal of the at least one physiological parameter, and generating second alarm information which corresponds to a second alarm, when the physiological parameter signal of the at least one physiological parameter is determined to satisfy a second alarm rule;

presenting, in a combined alarm mode, the first alarm information and the second alarm information, when the first alarm is associated with the second alarm.

In a preferable embodiment, the combined alarm mode includes adding an associated character string to the first alarm information and the second alarm information, so as to form a single piece of combined alarm information for presentation;

wherein the associated character string represents that the second alarm accompanies with the first alarm.

In a preferable embodiment, the first alarm information is presented at a first alarm level, and the single piece of combined alarm information is presented at a second alarm level, wherein the second alarm level is higher than the first alarm level.

According to the patient monitoring device and the alarm method for patient monitoring of the above-mentioned embodiments, when detecting that a physiological parameter of the patient simultaneously satisfy a first alarm rule and a second alarm rule, an alarm presentation mode of a single alarm, which alarm is generated by satisfying only the first alarm rule, is upgraded. In such a way, the risk of the single alarm, which risk becomes higher due to other associated factors, is presented in a more targeted manner, thereby helping medical staff to assess physiological and pathological state of the patient, and promoting the medical staff to implement intervention appropriately for the patient in a more timely manner.

BRIEF DESCRIPTION OF THE DRAWINGS

In order to provide a clearer explanation of the scheme in this disclosure, a brief introduction is given below to accompanying drawings required in the description of the embodiments of this disclosure. It is evident that the accompanying drawings are some embodiments of this disclosure. For those skilled in the art, other accompanying drawings can be obtained based on these drawings without creative labour.

DESCRIPTION OF THE PREFERRED EMBODIMENTS

Unless otherwise defined, all technical and scientific terms used herein have the same meaning as commonly understood by technicians in the technical field to which this disclosure belongs. The terms used in the description of this disclosure are only for the purpose of describing specific embodiments and are not intended to limit this disclosure. Terms "including" and "having" in the description and claims of this disclosure and the above-mentioned description for drawings, and any variations thereof are intended to cover non-exclusive inclusions. The terms "first", "second", etc., in the description and claims of this disclosure or the above-mentioned drawings are used to distinguish different objects, rather than to describe a specific order or technical meaning. The "connection" and "coupling" mentioned in this disclosure include direct and indirect connection(s) (coupling(s)), unless otherwise specified.

In addition, the features, operations, or characteristics described in the description may be combined in any appropriate manner to form various embodiments. At the same time, sequence(s) for steps or actions in the method description can also be exchanged or adjusted in a manner obvious to one skilled in the art. Therefore, the various sequences in the description and the drawings are only for the purpose of clearly describing a certain embodiment, and do not mean that they are necessary sequences. Unless it is otherwise specified that one of the sequences must be followed.

This disclosure is further described in detail below through specific embodiments in combination with the accompanying drawings. In the following embodiments, many details are described to enable this disclosure to be better understood. However, those skilled in the art can easily realize that some of the features may be omitted in different situations, or may be replaced by other elements, materials, or methods. In some cases, some operations associated with this disclosure are not shown or described in the description. This is to avoid the core part of this disclosure being overwhelmed by excessive description. For those skilled in the art, it is not necessary to describe these related operations in detail. They can fully understand the related operations based on the description in the disclosure and the general technical knowledge in the field.

Figure 1:
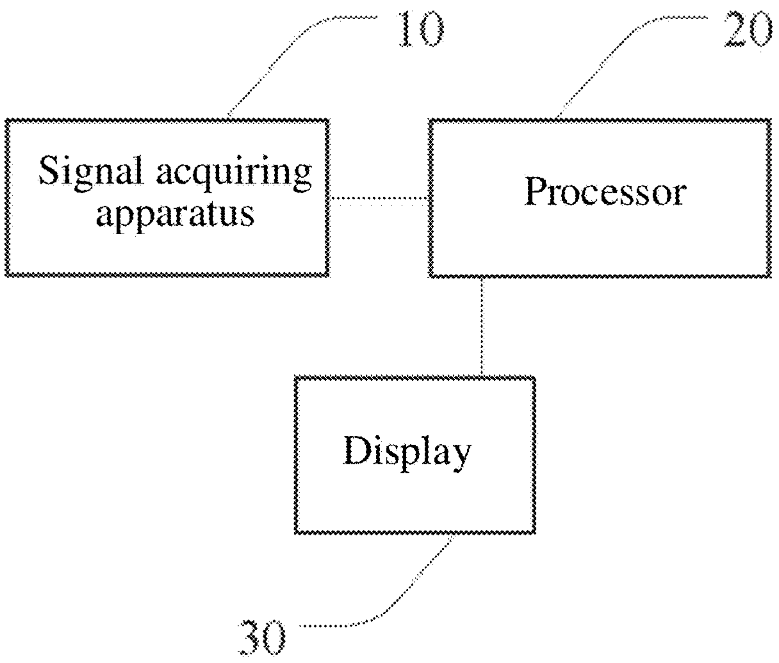
FIG. 1 is a system block diagram for an embodiment of a patient monitoring device provided by this disclosure.

As shown in FIG. 1, a patient monitoring device provided by this disclosure includes a signal acquiring apparatus 10, a processor 20 and a display 30. The display 30 is designed to output information, for example, to output visual information. The display 30 may be a display having only a display function, or may be a touch display.

The signal acquiring apparatus 10 is configured to acquire a physiological parameter signal, for example, to acquire a physiological parameter signal which corresponds to at least one physiological parameter of a patient, wherein the physiological parameter may also be referred to as a vital sign parameter. When the acquired physiological parameter signal includes more than two physiological parameters, in order to distinguish the two or more physiological parameters, a first physiological parameter and a second physiological parameter can be used, respectively. Correspondingly, a first physiological parameter signal and a second physiological parameter signal can be used to represent the physiological parameter signals corresponding to the two different physiological parameters, respectively.

The patient monitoring device may be any one of a monitor, a local central station, a remote central station, a cloud service system, and a mobile terminal, and the corresponding signal acquiring apparatus 10 acquires the physiological parameter signal in different ways. For example, if the patient monitoring device is a monitor, the signal acquiring apparatus 10 may use a sensor to monitor a physiological parameter of the patient and obtain a physiological parameter signal which corresponds to the physiological parameter. The physiological parameter may include various vital sign parameters, such as electrocardiogram, respiration, non-invasive blood pressure, blood oxygen saturation, pulse, body temperature, invasive blood pressure, end-respiratory carbon dioxide, respiratory mechanics, anesthetic gas, cardiac output, bi-spectral index, etc. The physiological parameter signal may be an original acquired electrical signal, and the corresponding physiological parameter signal may be visualized on the display 30 by at least one of numerical value(s), waveform(s), and a trend of change for waveform(s). For another example, the patient monitoring device may be a local central station, a remote central station, a cloud service system, or a mobile terminal, then the signal acquiring apparatus 10 is a communication device or a communication interface for communicating with a monitor to acquire the above-mentioned physiological parameter signal from the monitor. Alternatively, the patient monitoring device can also be a local central station, a remote central station, a cloud service system or a mobile terminal, then the signal acquiring apparatus 10 is a communication device or a communication interface, which is configured to communicate with a monitor, so as to obtain from the monitor, an original signal which is acquired by a sensor of the monitor; perform calculation(s) on the original signal, so as to obtain a physiological parameter signal which corresponds to the physiological parameter; and transfer the obtained physiological parameter signal to the monitor.

The processor 20 can be configured to process a physiological parameter signal of at least one physiological parameter, and generate a first alarm when determining that the physiological parameter signal of the at least one physiological parameter satisfies a first alarm rule. The processor 20 can analyse the physiological parameter signal to determine whether it satisfies a preset first alarm rule. The first alarm rule can be stored in a memory that cooperates with the processor 20 and can be read or called by the processor 20.

Taking a blood oxygen saturation parameter as an example, the processor 20 calculates a current value of blood oxygen saturation according to an analysis on a blood oxygen saturation signal. The corresponding first alarm rule may be, for example, an alarm rule for extremely-low blood oxygen saturation. The alarm rule for extremely-low blood oxygen saturation may be specifically explained as that a blood oxygen saturation value is less than an extremely-low threshold of blood oxygen saturation (e.g., 80%). When the monitored blood oxygen saturation value is less than the extremely-low threshold of blood oxygen saturation, the processor 20 determines that the blood oxygen saturation signal satisfies the alarm rule for extremely-low blood oxygen saturation, and generates a first alarm, namely, an alarm for extremely-low blood oxygen saturation. Similarly, the first alarm rule may also be, for example, an alarm rule for too-low blood oxygen saturation, and the alarm rule for too-low blood oxygen saturation may be specifically explained as that a blood oxygen saturation value is less than a too-low threshold of blood oxygen saturation (e.g., 90%). When the monitored blood oxygen saturation value is less than the too-low threshold of blood oxygen saturation, the processor 20 determines that the blood oxygen saturation signal satisfies the alarm rule for too-low blood oxygen saturation, and generates a first alarm, namely, an alarm for too-low blood oxygen saturation.

Further taking the blood oxygen saturation parameter as an example, the processor 20 further calculates a current value of blood oxygen saturation according to an analysis on a blood oxygen saturation signal. The corresponding first alarm rule may be, for example, an alarm rule for extremely-low blood oxygen saturation. The alarm rule for extremely-low blood oxygen saturation may be specifically explained as that a blood oxygen saturation value is less than an extremely-low threshold of blood oxygen saturation (e.g., 80%). When the monitored blood oxygen saturation value is less than the extremely-low threshold of blood oxygen saturation, the processor 20 determines that the blood oxygen saturation signal satisfies the alarm rule for extremely-low blood oxygen saturation and generates a first alarm, namely, an alarm for extremely-low blood oxygen saturation. The first alarm can also be an alarm for too-low arterial pressure, an alarm for respiratory suffocation, an alarm for extreme tachycardia, an alarm for extreme bradycardia, etc. The corresponding first alarm rules can be an alarm rule for too-low arterial pressure, an alarm rule for respiratory suffocation, an alarm rule for extreme tachycardia, an alarm rule for extreme bradycardia, etc. For more examples, please refer to the multiple first alarms listed in the first column of Tables 1-3. The first alarm rules corresponding to the first alarms in the examples in the tables are not described one by one here.

When the processor 20 generates the first alarm, the display 30 presents first alarm information in a predetermined first alarm area, wherein the first alarm information represents the first alarm. The first alarm information may be an alarm character string. Taking the alarm for extremely-low blood oxygen saturation (alarm for extremely-low SpO2) as an example, when an alarm for extremely-low SpO2 is generated, the display 30 displays a character string such as "Extremely-low SpO2" in a predetermined first alarm area. In this disclosure, "representing first alarm" does not limit a specific physical location and area occupied by the first alarm area on the display. The first alarm information is presented in a first presentation mode. In a specific example, the first presentation mode includes displaying the first alarm information in the first alarm area with a first background color. For example, if the first alarm is a medium-level alarm, the first alarm information can be displayed in the first alarm area with a medium-level alarm color (such as yellow). Specifically, taking the alarm for extremely-low SpO2 as an example, the alarm character string of "Extremely-low SpO2" may be displayed in the first alarm area with a background color corresponding to a high-level alarm (e.g., red). When only the first alarm exists, the display 30 may present the first alarm in a presentation mode corresponding to a severity level to which the alarm belongs.

The processor 20 is further configured to control the display 30 to display the first alarm information in a second presentation mode, when determining that the physiological parameter signal of at least one physiological parameter simultaneously satisfies the first alarm rule and the second alarm rule, wherein the second alarm rule is different from the first alarm rule, and the second presentation mode is an upgrade based on the first presentation mode. Specifically, when the monitored physiological parameter signal continues to be in a state of satisfying the first alarm rule, the first alarm information continues to be presented in the first presentation mode. At this time, if the monitored physiological parameter signal also satisfies the second alarm rule, according to general practice, an independent second alarm is to be generated and presented separately based on the physiological parameter signal which satisfies the second alarm rule. This disclosure upgrades the presentation mode of the first alarm information to more intuitively remind medical staff that the first alarm indicates that the physiological state of the patient has become more serious due to an existence of the second alarm, thereby more intuitively and timely reminding medical staff that the pathological risk of the patient may increase, so that timely intervention can be made on the patient.

The first alarm rule or the second alarm rule may include an alarm rule for exceeding a threshold, that is, the physiological parameter exceeds an alarm threshold. Alternatively, the first alarm rule or the second alarm rule may also include an alarm rule for an event, that is, an alarm rule for an abnormal event, wherein the alarm rule for an abnormal event is configured to determine whether the patient is in an abnormal state, such as whether the patient is in any one or more of respiratory suffocation, possible shock, atrial fibrillation, arrhythmia, etc.

It is worth mentioning that in this disclosure, the second presentation mode is an upgrade based on the first presentation mode, that is, it refers to a display mode that is more noticeable to user than an alarm display mode of the first presentation mode, including but not limited to, occupying a larger area to display the alarm, displaying the alarm by continuously flashing the alarm on the screen, displaying the alarm with brighter or thicker background color, etc.

The second presentation mode may be any display mode that is more noticeable to the user than the first presentation mode. In one embodiment, the first presentation mode includes displaying the first alarm information in the first alarm area with a first background color, and the second presentation mode includes displaying the first alarm information in the first alarm area with a second background color, wherein the second background color has a stronger warning effect than the first background color. For example, please refer to FIG. 2, which is an alarm presentation diagram of an embodiment of the patient monitoring device provided by this disclosure, which shows that the alarm for too-low SpO2 is presented in an upgraded presentation mode to prompt medical staff that an alarm for high RR accompanies with the alarm for too-low SpO2 at the same time. The display area 200 illustrates a main interface of the display 30, which interface can be used to display the physiological parameter signal in real time, such as wave-forms, values of physiological parameter(s), etc. Various information can be displayed in different areas of the main interface. For example, the first alarm area 201 can be located in a corner or other position of the main interface. As described above, when only an alarm for too-low SpO2 exists, because the alarm for too-low SpO2 is set as a medium-level alarm in an alarm setting, this alarm can be presented by displaying the alarm character string of too-low SpO2 in the first alarm area 201 with a first background color, such as yellow. When the alarm for too-low SpO2 is accompanied by the alarm for high RR, the alarm character string of too-low SpO2 (that is, the first alarm information in this embodiment) continues to be presented in the first alarm area 201 but in a second background color, wherein the second background color has a stronger warning effect than the first background color, such as orange, red, etc., thereby achieving an upgraded presentation of the first alarm information of the alarm for too-low SpO2.

Figure 3:
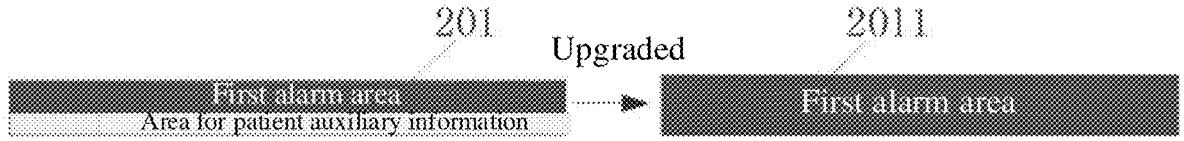
FIG. 3 is a diagram for an enlarged first alarm area of an embodiment in a patient monitoring device provided by this disclosure.

However, it is not limited to this. For example, as shown in FIG. 3, the first alarm area 201 can be enlarged and the first alarm information can be displayed in the enlarged first alarm area 2011. Specifically, the first alarm area 201 can be enlarged to cover one or more adjacent areas. The adjacent one or more areas may include at least part of at least one of following areas: another alarm area, an area for patient auxiliary information, an area for patient identity information (such as areas displaying bed number and patient name). Said another alarm area may be an alarm area for a device alarm or for a technical parameter alarm. The enlarging may refer to enlarging of an area which is occupied by the background color, or enlarging of an area which is occupied by the alarm character string and/or background color, which correspond(s) to the alarm information, so as to upgrade the alarm.

In another example, the first alarm information may also be displayed in the first alarm area 201 with a flashed first background color or a flashed second background color. Since being flashed itself has a stronger warning effect than not being flashed, the presentation mode of the first alarm information can be upgraded only by adding the flashing or increasing a flashing frequency. Therefore, the background color can be maintained as the first background color. Of course, the presentation mode of the first alarm information can also be upgraded by flashing a second background color to achieve a stronger warning effect. In other examples, the first alarm information may also be displayed in a second alarm area outside the first alarm area. For example, the first alarm information may be displayed in a pop-up window in a second alarm area outside the first alarm area on the main interface of the display. Alternatively, the second alarm area may also be a display area embedded in the main interface. The first alarm information of the first alarm area 201 may be displayed at the same time, or not displayed.

In another example, the second presentation mode may further include simultaneously displaying the second alarm information and the first alarm information in an associated combination mode, wherein the second alarm information represents that the physiological parameter signal of the at least one physiological parameter satisfies the second alarm rule. Upgrading the alarm presentation mode by adding the second alarm information on the basis of the first alarm information can also be regarded as presenting the first alarm and the second alarm in a combined alarm mode, so that it can be more intuitive to see that the second alarm accompanies with the first alarm.

Please refer to FIG. 2 again. In the first alarm area 201, the alarm character string "too-low SpO2" corresponding to the alarm for too-low SpO2 and the alarm character string "too-high RR" corresponding to the alarm for too-high RR are combined into combined alarm information. For example, the alarm character string "too-high RR" is placed after "too-low SpO2" to form combined alarm information. The first alarm area 201 may have the same background color as the first presentation mode, or the background color may be upgraded, for example, from yellow to red.

While the first alarm information is being updated and presented, the accompanied second alarm may also be displayed separately, for example, the second alarm information may be displayed separately in the second alarm area 202.

Figure 2:
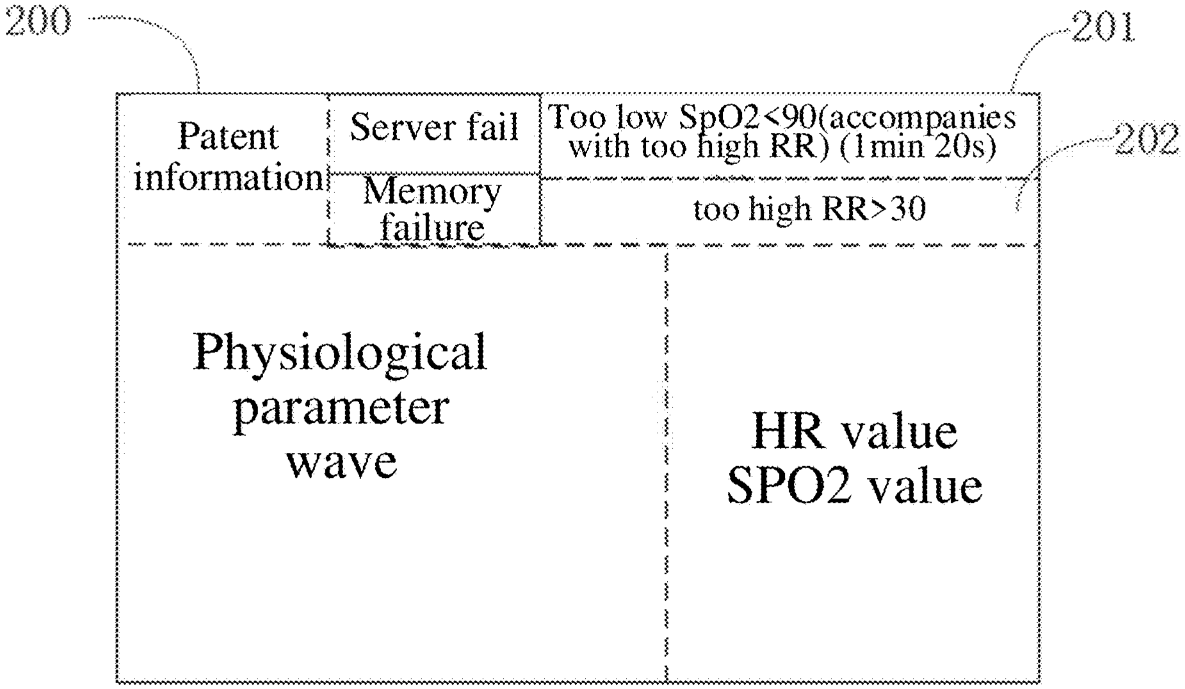
FIG. 2 is a diagram for alarm presentation of an embodiment in a patient monitoring device provided by this disclosure.

The first alarm area 201 and the second alarm area 202 may be arranged side by side from up to down as shown in FIG. 2, or they may be arranged side by side for left to right.

In order to more clearly show an accompanied relationship between the first alarm and the second alarm, the first alarm information and the second alarm information may be associated with each other through an associated character string to form combined alarm information, wherein the associated character string represents that the second alarm information accompanies with the first alarm information. The associated character string can be one of word(s), symbol(s), and mark(s), or any combination thereof. Optionally, symbol(s) include(s) but is(are) not limited to one or more of a comma, "&" symbol, bracket, or semicolon, word(s) include(s) but is(are) not limited to conjunction(s), such as "and", "with", "accompanies with", etc. For example, in FIG. 2, the alarm character string "Too-high RR" and the alarm character string "too-low SpO2" are connected by the words "accompanies with". The associated character string can also be "along with", "accompanied by", "with", "and", "accompanies with", "along with", comma, "&" symbol, bracket, etc.

It should be understood that the associated character string is not limited to the examples disclosed in this disclosure, and may be any other character string as long as it can reflect the accompanied relationship between the first alarm and the second alarm.

Adding the accompanied second alarm information to the first alarm information, is also an upgraded presentation of the first alarm information. By combining two or more alarm information, two related alarms can be presented in a related combination mode (that is, in the combined alarm mode), which can more intuitively remind medical staff of the increased pathological risk of patient caused by the simultaneous occurrence of two or more related alarms.

It is worth mentioning that, in this disclosure, "a combined alarm" can be understood as presenting the first alarm information and the second alarm information in combination through an associated character string, such as hyphen(s) (such as commas, semicolons, etc.), conjunction(s) (such as "and", "with", "accompanied by" . . . , etc.), so as to form "combined alarm" information. The combined alarm information can present more specific alarm information to medical staff in multiple dimensions, so that medical staff can understand the condition of the patient more clearly. The first alarm information and the second alarm information associated with each other through the associated character string may be displayed on the display 30 only when duration(s) of the alarm(s) exceed(s) preset time length(s). In this way, the presentation of some alarm information in the case where the alarm rule is briefly satisfied but soon not satisfied on its own, can be ignored, so that medical staff can only focus on the alarm information, which requires more attention and is of long duration.

When the physiological parameter signal of at least one physiological parameter no longer satisfies the second alarm rule, the display 30 clears the second alarm information. If a third alarm that satisfies another alarm rule occurs at the same time, and the third alarm is also associated with the first alarm, the first alarm and the third alarm can continue to be presented in a combined alarm mode.

Figure 4:
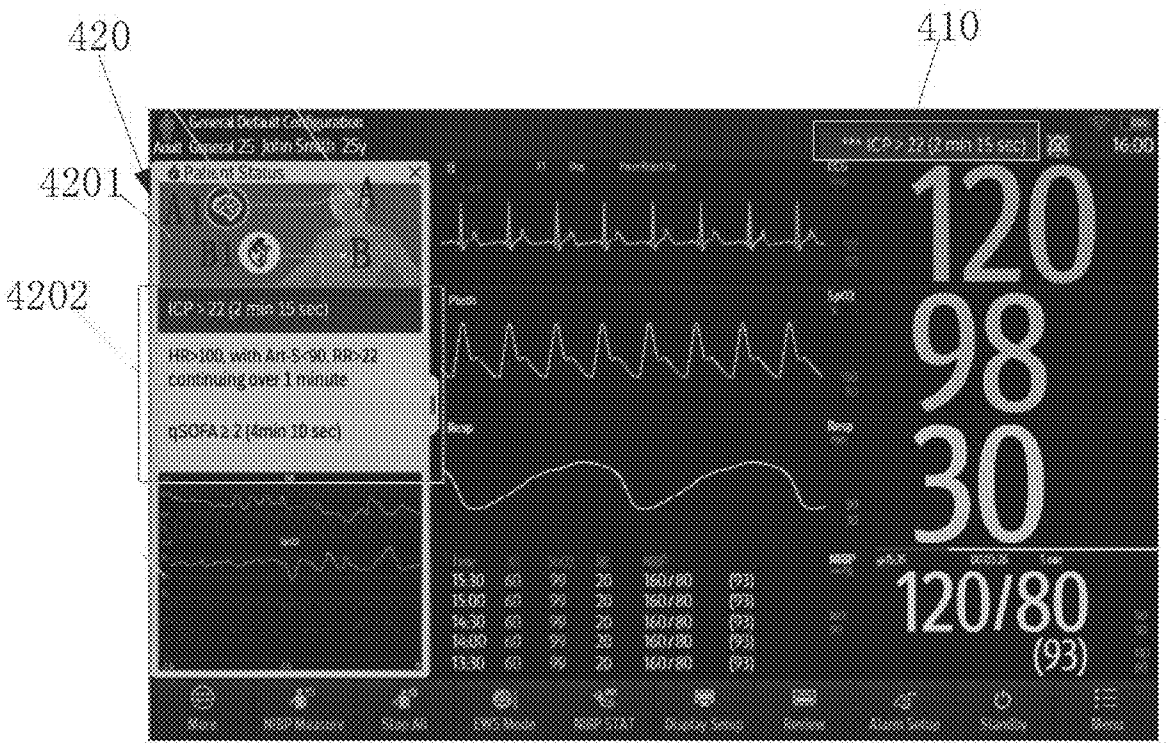
FIG. 4 is a diagram for alarm presentation of another embodiment in a patient monitoring device provided by this disclosure.

Please refer to FIG. 4, which is a schematic diagram of alarm presentation of another embodiment of a patient monitoring device provided by this disclosure, in which the second alarm information and the first alarm information are simultaneously displayed in a second alarm area in an associated combination mode, wherein the first alarm area and the second alarm area are independent of each other. For example, the second alarm area can be displayed independently in an area which is different from the first alarm area on the main interface of the display. The second alarm area can be in the form of a pop-up window which covers a part of the display area on the main interface, or can be a display window or display area embedded in the main interface. No specific limitation is made here, and some details about FIG. 4 are described below.

In order to enable the user to pay attention to more dangerous alarm(s), the first alarm area and the second alarm area can be distinguished by different background colors. For example, the background color of the first alarm area has a stronger warning effect than the background color of the second alarm area, and the accompanied alarm and the separate second alarm can be distinguished and warned, so as to more clearly remind medical staff of existence of the accompanied second alarm without affecting the medical staff to quickly and promptly check the separate second alarm information due to other clinical needs.

Figure 5:
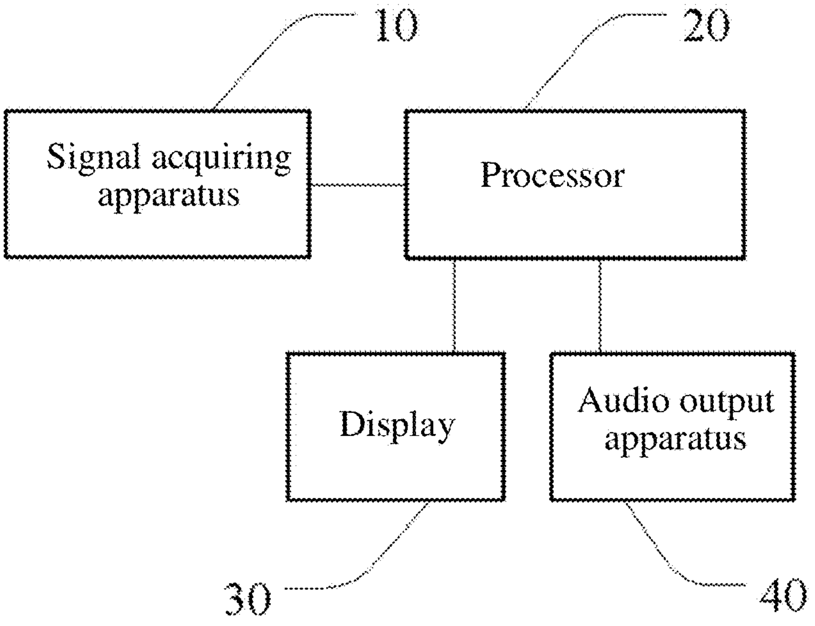
FIG. 5 is a system block diagram for another embodiment of a patient monitoring device provided by this disclosure.

Please refer to FIG. 5, which shows a block diagram of another embodiment of a patient monitoring device provided by this disclosure. Compare with the block diagram of the patient monitoring device system shown in FIG. 1, an audio outputting apparatus 40 is further included. The audio outputting apparatus 40 can output an alarm sound which corresponds to a first alarm level, while the first alarm information is presented in the first presentation mode, and can also output an enhanced alarm sound, while the first alarm information is presented in the second presentation mode. Alternatively, the audio outputting apparatus 40 can also not output an alarm sound, while the first alarm information is presented in the first presentation mode, and output an alarm sound, while the first alarm information is presented in the second presentation mode.

The foregoing mainly uses a situation where the alarm for too-low SpO2 is accompanied by the alarm for high RR to explain some embodiments of upgrading the presentation of the alarm for too-low SpO2, wherein the alarm for too-low SpO2 is an alarm associated with the blood oxygen saturation parameter, and the blood oxygen saturation signal can be analysed to determine whether it satisfies the alarm rule for too-low SpO2, while the alarm for high RR is an alarm associated with the respiratory parameter, and the respiratory signal can be analysed to determine whether it satisfies the alarm rule for high RR. That is to say, the first alarm rule and the second alarm rule in the foregoing example are respectively associated with different physiological parameters, and the corresponding first alarm and second alarm are also associated with different physiological parameters. However, the first alarm in this disclosure is not limited to the alarm for too-low SpO2, nor to the alarm associated with the blood oxygen saturation parameter. The first alarm and the second alarm may also be associated with the same physiological parameter, or the first alarm is associated with a first physiological parameter, and the second alarm is associated with one or more physiological parameters which is(are) different from the first physiological parameter.

Please refer to Table 1, which shows some conditions and modes for upgrading and presenting first alarm information in a list form.

TABLE 1

| First alarm | Upgrade condition | Upgraded level | Additional character string for alarm |
|---|---|---|---|
| Alarm for respiratory suffocation | Duration of alarm exceeds 20 s | High level | None |
| Alarm for respiratory suffocation | Duration of alarm exceeds 40 s | Exclusive | None |
| Alarm for extreme tachycardia | Duration of alarm exceeds 120 s | Exclusive | None |
| Alarm for extreme bradycardia | Duration of alarm exceeds 120 s | Exclusive | None |
| Alarm for extremely-low SpO2 | Duration of alarm exceeds 20 s | Exclusive | None |
| Alarm for extremely-low SpO2b | Duration of alarm exceeds 20 s | Exclusive | None |
| Alarm for possible shock state (HR > 100, with Art-Sys < 90, RR > 22 rpm; or (HR > 100, with ΔArt-Sys [↓30 mmHg, RR > 22 rpm | Duration of alarm exceeds 300 s | Exclusive | |

The 2nd to 7th rows of the 1st column in the table respectively illustrate four first alarms: an alarm for respiratory suffocation, an alarm for extreme tachycardia, an alarm for extreme bradycardia, and an alarm for extremely-low SpO2. The 2nd to 7th rows of the 2nd column correspond to upgrade conditions for upgrading the first alarms in the same row, and the upgrade conditions are that a duration of a first alarm exceeds a preset threshold, that is, the second alarm rule is that a duration, in which the first alarm rule is satisfied, exceeds the preset threshold, and the 3rd column corresponds to the upgraded alarm level. Taking the first alarm as an alarm for respiratory suffocation as an example, the alarm for respiratory suffocation is generated based on the respiratory parameter signal, and the corresponding alarm rule for respiratory suffocation is also associated with the respiratory parameter. When the processor analyses the respiratory parameter signal and determines that the respiratory parameter signal satisfies the alarm rule for respiratory suffocation, the alarm for respiratory suffocation is generated. When the alarm for respiratory suffocation occurs and continues for less than 20 s, the display 30 presents the first alarm information "respiratory suffocation" at a medium level or low level. When a duration of the alarm for respiratory suffocation exceeds a preset value of 20 s, it is equivalent to that the second alarm rule has been satisfied. The second alarm rule and the first alarm rule here are both associated with the same physiological parameter, that is, the respiratory parameter, wherein the second alarm rule can be expressed as a time length, in which the respiratory parameter signal continuously satisfies the first alarm rule, exceeds the preset value, so the column of the upgrade condition can essentially be regarded as a second alarm rule. When the upgrade condition or the second alarm rule is satisfied, the display 30 presents the first alarm at a relatively higher alarm level to indicate that the respiratory suffocation poses a higher risk to the patient due to prolonged duration, thereby attracting the attention of medical staff more promptly so that timely intervention can be provided to the patient.

The multiple first alarms recorded in the first column of Table 1 may be alarms associated with a blood oxygen saturation parameter, an electrocardiogram parameter, a respiratory parameter, or a blood pressure parameter, and the corresponding first alarm rules may be that a signal of blood oxygen saturation parameter exceeds an alarm threshold for the blood oxygen saturation parameter, an electrocardiogram parameter signal exceeds an alarm threshold for the electrocardiogram parameter, a respiratory parameter signal exceeds an alarm threshold of the respiratory parameter, and a parameter signal of a blood pressure exceeds the alarm threshold of the blood pressure parameter.

It should also be noted that an upgraded presentation level of the first alarm information only needs to be converted from a relatively low level to a relatively high level. For example, the upgraded level in the table is higher than the level before the upgrade. For example, if the upgraded level is a high level, then the level before the upgrade may be a medium level. For another example, if the upgraded level is exclusive, then the level before the upgrade may be medium level or high level. The "Exclusive level" shown in Table 1-3 is a more prominent alarm presentation mode than the "high level". For example, the alarm area for an alarm presentation mode of the "exclusive" level is larger than that for an alarm presentation mode of the "high level"; or a font in an alarm presentation mode of the "exclusive" level is enlarged, or other alarm presentation modes that can make the alarm more prominent are used in the alarm presentation mode of the "exclusive" level.

"Additional character string for alarm" in 4th column of Table 1 is displayed as "None", which means that after the first alarm satisfies the upgrade condition, no additional character string for alarm is added on the basis of the displayed first alarm information, and the original first alarm information is still displayed, for example, "alarm for extremely-low SpO2" is still displayed. Of course, in other examples, the duration of the first alarm can also be used as an additional alarm character.

Please refer to Table 2, which lists more examples of combined alarm upgrades, wherein the second alarm rule (i.e., upgrade condition) is associated with a second physiological parameter, and the first alarm rule is associated with a first physiological parameter. It may be that when the first physiological parameter satisfies the first alarm rule, and the second physiological parameter satisfies the second alarm rule, the alarm is presented in an upgraded mode, for example, in the combined alarm mode. Alternatively, the processor 20 is further configured to control the display 30 to simultaneously present the first alarm information and the second alarm information in an associated combination mode (wherein the associated combination mode can be understood as the combined alarm mode), when determining that the first physiological parameter satisfies the first alarm rule, and the second physiological parameter satisfies the second alarm rule. The second alarm rule includes: the second physiological parameter satisfies an alarm rule for exceeding a threshold and/or an alarm rule for an event; and duration(s) exceed(s) preset time length(s), in which duration(s) the second physiological parameter satisfies the alarm rule for exceeding a threshold and/or the alarm rule for an event. The first alarm information represents that the first physiological parameter satisfies the first alarm rule, and the second alarm information represents that the second physiological parameter satisfies the second alarm rule.

Similar to the situation that the alarm for too-low SpO2 accompanies with the alarm for high RR, described in the previous article, take the combination in which an alarm for too-low SpO2 accompanies with an alarm for high RR in the table as an example, such alarm combination is still a combined alarm, which is generated based on the signal of blood oxygen saturation parameter and the respiratory parameter signal. The difference is that only when: the monitored physiological parameter signal satisfies the first alarm rule (alarm rule for extremely-low SpO2, alarm rule for too-low SpO2, alarm rule for extremely-low SpO2b or alarm rule for too-low SpO2b), and satisfies the second alarm rule (such as alarm rule for too-high RR, or alarm rule for too-low RR); and a duration, in which the monitored physiological parameter signal satisfies the first alarm rule and the second alarm rule, exceeds a preset threshold, such as 120 s; the first alarm information (such as alarm for extremely-low SpO2, alarm for too-low SpO2, alarm for extremely-low SpO2b or alarm for too-low SpO2b) is presented in an upgraded mode. In other words, the accompanied alarm for too-high RR, which alarm continues less than 120 s may have little impact on the risk level of the patient and does not need to warn medical staff in a more noticeable way.

TABLE 2

| First alarm | Upgrade condition | Upgraded level | Additional character string for alarm |
|---|---|---|---|
| Alarm for too-low SpO2 | Alarm for too-high RR; and Both alarms continue over 120 s | High level | Accompanies with too-high RR |
| Alarm for too-low SpO2 | Alarm for too-low RR; and Both alarms continue over 120 s | High level | Accompanies with too-low RR |
| Alarm for extremely-low SpO2 | Alarm for too-high RR | High level (Exclusive) | Accompanies with too-high RR |
| Alarm for extremely-low SpO2 | Alarm for too-low RR | High level (Exclusive) | Accompanies with too-low RR |

Please refer to Table 3, which lists more combination alarms, wherein the first physiological parameter is a blood pressure parameter, the first alarm rule includes an alarm rule for too-low arterial pressure, the second physiological parameter is an electrocardiogram parameter, and the second alarm rule includes at least one of: an alarm rule for too-low HR, an alarm rule for bradycardia, an alarm rule for tachycardia, an alarm rule for atrial fibrillation, an alarm rule for ventricular rhythm, an alarm rule for bigeminy ventricular premature contraction, an alarm rule for trigeminy premature ventricular contraction, an alarm rule for too-high ST, an alarm rule for too-low ST, an alarm rule for a single ΔST that exceeds a threshold, and an alarm rule for multiple ΔSTs that exceed threshold(s).

TABLE 3

| First alarm | Upgrade condition | Upgraded level | Additional character string for alarm |
|---|---|---|---|
| Alarm for too-low arterial pressure | Alarm for too-low heart rate | High level | Accompanies with too-low heart rate |
| Alarm for too-low arterial pressure | Alarm for bradycardia | High level | Accompanies with bradycardia |
| Alarm for too-low arterial pressure | Alarm for Alarm for tachycardia | High level | Accompanies with tachycardia |
| Alarm for too-low arterial pressure | Alarm for a ΔST that exceeds a threshold | High level | Accompanies with a ΔST that exceeds a threshold |
| Alarm for too-low arterial pressure | Alarm for a single ΔST that exceeds a threshold | High level | Accompanies with a single ΔST that exceeds a threshold |
| Alarm for too-low arterial pressure | Alarm for multiple ΔSTs that exceed threshold(s) | High level | Accompanies with multiple ΔSTs that exceed threshold(s) |
| Alarm for too-low arterial pressure | Alarm for atrial fibrillation | High level | Accompanies with atrial fibrillation |
| Alarm for too-low arterial pressure | Alarm for ventricular rhythm | High level | Accompanies with ventricular rhythm |
| Alarm for too-low arterial pressure | Alarm for bigeminy ventricular premature contraction | High level | Accompanies with bigeminy ventricular premature contraction |
| Alarm for too-low arterial pressure | Alarm for trigeminy premature ventricular contraction | High level | Accompanies with trigeminy premature ventricular contraction |

Continuing to refer to FIG. 1, this disclosure also provides a patient monitoring device, with a block diagram which is the same as that of FIG. 1. Specifically, the patient monitoring device includes: a signal acquiring apparatus 10, which is configured to acquire a physiological parameter signal of at least one physiological parameter of a patient; a processor 20, which is configured to generate a first alarm when the physiological parameter signal of the at least one physiological parameter satisfies the first alarm rule, and generate a second alarm when the physiological parameter signal of the at least one physiological parameter satisfies the second alarm rule; and a display 30, which is configured to display first alarm information and second alarm information, wherein the first alarm information represents the first alarm, and the second alarm information represents the second alarm, and the display is further configured to output, in a combined alarm mode, the first alarm information and the second alarm information, when the physiological parameter signal of the at least one physiological parameter simultaneously satisfies the first alarm rule and the second alarm rule.

In one example, the combined alarm mode includes displaying the first alarm information and the second alarm information in combination through an associated character string, wherein the associated character string represents that the second alarm accompanies with the first alarm.

FIG. 4 is a diagram for alarm presentation of another embodiment in a patient monitoring device provided by this disclosure. In this embodiment, a variety of alarm information is presented in a unit for details of a patient state 4202 (i.e., the second alarm area), which is independent of the first alarm area 410. For example, a combined alarm K displayed as "HR>100 with Art-Sys<90, RR>22 continuing over 1 minute" is presented in a patient state window 420 floating on the main interface, which indicates that a current state of the patient is that a heart rate HR is greater than 100, accompanied by a systolic blood pressure Art-Sys which is less than 90 and a respiratory rate which is greater than 22, and this state has continued for more than 1 minute. This disclosure outputs multiple single alarms HR>100, Art-Sys<90, RR>22, which do not indicate that the patient is at serious risk when they occur separately, in the combined alarm mode to remind medical staff that the patient may be in a state of shock and requires immediate intervention. In this embodiment, the first alarm rule is that the heart rate is greater than an alarm threshold of heart rate (for example, an alarm threshold of heart rate is 100). The second alarm rule is that a duration, in which the systolic blood pressure is less than an alarm threshold of systolic blood pressure (for example, the alarm threshold of systolic blood pressure is 90) and the respiratory rate is greater than an alarm threshold of respiratory rate (for example, an alarm threshold of respiratory rate is 22), exceeds a preset time length. The patient monitoring device can determine whether the acquired physiological parameter signal satisfies the first alarm rule and the second alarm rule at the same time by monitoring the obtained blood pressure signal, respiratory signal and blood oxygen saturation signal, thereby outputting the first alarm information "HR>100" and the second alarm information "Art-Sys<90, RR>22 continuing over 1 minute" in a combined alarm, and the "with" in the combined alarm K can be regarded as an associated character string, which is configured to associate and combine the first alarm information with the second alarm information. In another embodiment, the combined alarm K may also be "HR>100, with ΔArt-Sys ↓30 mmHg and RR>22 rpm continuing for more than a preset time length", wherein the preset time length may be 60, 300 or other suitable values.

In addition, in the relatively fixed first alarm area 410 of the main interface, each single alarm can be displayed separately. For example, HR>100, Art-Sys<90, RR>22 can be scrolled and displayed in the first alarm area 410. Of course, the simultaneous occurrence of these single alarms can also be displayed in the combined alarm mode in the first alarm area 410.

On the basis of separate outputs of the single alarms, the first alarm information and the second alarm information are simultaneously presented in the combined alarm mode, which makes it easier for medical staff to pay attention to the occurrence of the combined alarm.

In order to facilitate the doctor to observe the patient state, the patient state window 420 shown in FIG. 4 can also present the patient state in the form of a human body diagram, wherein the patient state can be the patient state obtained by the processor through analysing the physiological parameter signal according to preset rule(s), wherein the patient state includes one or more of: an overall state of the patient, a physiological system state, an organ state, a physiological part state, and a tissue state. The display is further configured to present the patient state in the form of a human body diagram, and present at least one item of alarm information in a combined alarm mode, which information is associated with the patient state, such as the first alarm information and the second alarm information which are outputted in the combined alarm mode described above.

After acquiring the patient data (including at least a physiological parameter signal of at least one physiological parameter of the patient, and may also including treatment device data, drug administration data, laboratory test data, imaging data, and diagnostic data, etc.), the processor 20 analyses the patient data according to a preset rule, so as to obtain the patient state. For example, the processor 20 analyses the patient data based on a state determination rule database stored in the memory. The state determination rule database stores rules for determining the patient state. These rules can be preset by the user, or can be automatically generated through big data learning. The automatically generated rules can be processed manually to eventually form recognized rules in the rule base.

Then, on the display 130, the patient state is presented in the form of a human body diagram, and at least one item of alarm information, which is associated with the patient state, is presented in the form of text or graphic in the combined alarm mode. For example, a dedicated patient state window 420 may be configured to display the patient state, and display, in the combined alarm mode, the at least one item of alarm information which is associated with the patient state. Here, the "dedicated patient state window" can be understood as a window that is different and independent from common areas or windows that display patient data, alarm data, etc., on a medical device, such as a monitor. Specifically, the patient state window 131 includes a unit for a human body diagram 4201 and a unit for details of a patient state 4202, wherein the unit for a human body diagram 4201 displays the patient state, such as one or more of an overall state of the patient, a physiological system state, an organ state, a physiological part state, and a tissue state. The unit for details of a patient state 4202 displays, in the combined alarm mode, at least one item of alarm information which is associated with the patient state, such as an alarm which is generated, when at least one physiological parameter, which parameter is associated with the patient state, satisfies a preset alarm condition, and a duration of the alarm, etc. In an embodiment of this disclosure, the patient data is analysed, so as to obtain the patient state and the at least one item of alarm information which is associated with the patient state and presented in the combined alarm mode; and the patient state is graphically presented to the medical staff in the form of the human body diagram, while the at least one item of alarm information, which is associated with the patient state, is further presented to the medical staff via text or graph in the combined alarm mode, so that the medical staff can intuitively and clearly know the patient state and related alarm condition, thereby facilitating the medical staff to quickly take treatment measure according to the patient state.

In an embodiment of this disclosure, the unit for a human body diagram 4201 can present a human body diagram, and present the patient state by marking the human body diagram. On the human body diagram, when the patient state includes the overall state of the patient, the entirety human body diagram is marked. When the patient state includes one or more of the physiological system state, the organ state, the physiological part state, and the tissue state, one or more of physiological system, organ, physiological part, and tissue, which corresponds/correspond to the patient state, are marked. Therefore, the human body diagram may be a complete human body diagram (including a complete human body) or at least a partial human body diagram (including at least a partial human body). By presenting the human body diagram and marking the human body diagram to present the patient state, medical staff can very intuitively view the overall state of the patient or the state of certain physiological system, organ, physiological part, tissue, etc., of the patient.

In an embodiment of this disclosure, the human body diagram can be marked via at least one of graph information, symbol information, color information, and text information, which is located on or adjacent to the human body diagram, thereby presenting the patient state. The patient state may include whether one or more of the overall state of the patient, physiological system state, organ state, physiological part state and tissue state is/are abnormal or not, and one or more of an abnormality level, a criticality level, and a nursing level. An exemplary description is given below in conjunction with FIG. 4.

As shown in FIG. 4, in this example, the unit for a human body diagram displays the human body diagram including an upper body and a head, in which relevant physiological parts A and B (brain and heart, respectively) are marked on the human body diagram, indicating that states of the physiological parts A and B have been analysed based on the acquired patient data. Usually, these states are abnormal, because marking the abnormal state is more meaningful. However, these states may also be normal, which depends on whether the patient state window is permanently displayed or is just displayed when abnormal. This is to be described later.

In addition, state information A1 and B1 of the physiological parts A and B are displayed adjacent to the human body diagram (peripheral area). In the example shown in FIG. 4, the state information A1 and B1 includes a drawn structure of the physiological part (the brain and the heart, respectively) and the state of the physiological part which is presented in color information. Here, since it is a grayscale image, the display effect is not obvious. In practical applications, for example, red lines, red fills, etc., can be configured to present abnormalities of the physiological parts, and a shade of red color can also be configured to present abnormality levels. In this example, the human body diagram is marked with graph information and color information to present the patient state. The patient state is presented in the peripheral area of the human body diagram. In addition, whether the physiological part of the patient is abnormal, and the abnormality level of the physiological part are presented. In other examples, the state of a certain physiological part of the patient can also be presented via other ways and other locations, such as via symbolic information and/or text information. The location of presentation may not be the peripheral area of the human body diagram, but at the human body diagram. In addition, other state of a certain physiological part can also be presented, such as criticality level and/or nursing level, etc. Furthermore, in the example of FIG. 4, the state of a specific physiological part of the patient is shown. But this is only exemplary, and the overall state of the patient may also be shown, such as the criticality level and/or nursing level of the patient, etc. Similarly, the overall state of the patient can also be presented via at least one of symbol information, color information, and text information. In this case, the human body diagram may be the entirety human body, or the human body diagram may not be included. For example, when the patient is normal, text "Normal" is displayed in a green background, when the patient is critical, text "Critical" is displayed in a red background. Similarly, the physiological system state, organ state, tissue state of the patient, etc., can also be presented in a similar manner as described above.

In an embodiment of this disclosure, presenting in the combined alarm mode, by the unit for details of a patient state 4202, at least one item of alarm information which is associated with the patient state, may include combining an alarm for exceeding a threshold of and/or an alarm for an event, for the at least one physiological parameter signal, which parameter is associated with the patient state, with duration(s) of the alarm for exceeding a threshold and/or the alarm for an event; and presenting the alarm for exceeding a threshold and/or the alarm for an event and the duration(s) of the alarm for exceeding a threshold and/or the alarm for an event. In addition, a duration of an alarm can also be other time information of said alarm, such as interval time of said alarm, occurrence frequency within unit time, etc. Wherein it is also possible that, when the duration(s) of the alarm(s) exceed(s) preset time length(s), the alarm for exceeding a threshold of and/or the alarm for an event, for the at least one physiological parameter signal, which parameter is associated with the patient state, are/is combined with the preset time length(s), and then presented with the preset time length. Wherein the alarm for exceeding a threshold refers to an alarm which satisfies an alarm rule for exceeding a threshold. The alarm rule for exceeding a threshold may include that a certain parameter value exceeds its preset threshold. The alarm for an event refers to an alarm for an abnormal event. For example, an alarm for an abnormal event is outputted when a patient is determined to be in an abnormal state by analysing one or more physiological parameters. At least one item of alarm information, which is associated with the patient state and presented in the combined alarm mode, can be presented via text. The alarm and its time information can be presented in a combined manner, so as to jointly reflect one or more of the overall state of the patient, the same physiological system state, the same organ state, the same physiological part state, and the same tissue state. Herein, the alarm and time information can be presented in a combined manner, can be understood as using hyphen(s) (such as commas, semicolons, etc.), connecting word(s) (such as "and", "also", "with", etc.) to combine and present the alarm and alarm-related time information, so as to form combined alarm information.

Compared with non-combined alarm information that does not include time information, the combined alarm information can present more detailed alarm information to medical staff in multiple dimensions. So that medical staff can have a clearer understanding of the patient condition. It should be understood that the associated character string is not limited to the examples disclosed in this disclosure, and may be any other character string as long as it can reflect that the presented information is one or more alarms and time information thereof. Wherein it is possible to display in the combined alarm mode, on the display 30, the at least one item of alarm information, which is associated with the patient state, when the duration of the alarm exceeds a preset time length. In this way, the presentation of some alarm information in the case where the alarm rule is briefly satisfied but soon not satisfied on its own, can be ignored, so that medical staff can only focus on the alarm information, which requires more attention and is of long duration.

In another embodiment, the physiological parameter signal of at least one physiological parameter signal of the patient includes a first physiological parameter signal and a second physiological parameter signal, and the processor 20 is further configured to control the display to simultaneously present the first alarm information and the second alarm information in an associated combination mode, when determining that the first physiological parameter satisfies the first alarm rule and the second physiological parameter satisfies the second alarm rule. For example, the second alarm rule includes: the second physiological parameter signal satisfies the alarm rule for exceeding a threshold and/or the alarm rule for an event; and duration(s) exceed(s) preset time length(s), in which duration(s) the second physiological parameter satisfies the alarm rule for exceeding a threshold and/or the alarm rule for an event. Alternatively, the second alarm rule includes: the second physiological parameter signal satisfies the alarm rule for exceeding a threshold and/or the alarm rule for an event. The first alarm information represents that the first physiological parameter satisfies the first alarm rule, and the second alarm information represents that the second physiological parameter satisfies the second alarm rule. At least one item of alarm information, which is associated with the patient state and presented in the combined alarm mode, can be presented via text. The first alarm rule may be an alarm rule for exceeding a threshold and/or an alarm rule for an abnormal event, which alarm rule(s) is(are) associated with the first physiological parameter; wherein a first alarm for exceeding a threshold and/or a first alarm for an abnormal event, occurs simultaneously with a second alarm for exceeding a threshold and/or a second alarm for an abnormal event. In this embodiment, the unit for details of a patient state 4202 presents two alarms which respectively correspond to two physiological parameter signals, wherein the two alarms are presented in a combined mode, and jointly reflect one or more of the overall state of the patient, the same physiological system state, the same organ state, the same physiological part state, and the same tissue state. Here, two alarms are presented as a group, which is also a kind of combined alarm information, and can present related alarm information to medical staff, so that medical staff can understand the patient condition more clearly.

Furthermore, the aforementioned presenting, via text, at least one item of alarm information, which is associated with the patient state and presented in the combined alarm mode, includes combing and presenting followings: a first alarm for exceeding a threshold and/or a first alarm for an abnormal event, for a first physiological parameter, which parameter is associated with the patient state; a second alarm for exceeding a threshold and/or a second alarm for an abnormal event, for a second physiological parameter, which parameter is associated with the patient state; and a duration in which: the first alarm for exceeding a threshold and/or the first alarm for an abnormal event, and the second alarm for exceeding a threshold and/or the second alarm for an abnormal event, simultaneously occur. In this embodiment, the unit for details of a patient state 4202 presents two alarms which respectively correspond to two physiological parameters and the durations of the two alarms, which jointly reflect one or more of the overall state of the patient, the same physiological system state, the same organ state, the same physiological part state, and the same tissue state. Here, two alarms and the durations thereof are presented as a group, which is also a kind of combined alarm information, and can present related alarm information to medical staff, so that medical staff can understand the patient condition more clearly.

As shown in FIG. 4, the first alarm area 410 includes information of intracranial pressure (ICP), including two types of information, namely an alarm rule and the time information associated with an alarm, that is-ICP has been greater than 22 mmHg for 2 minutes and 15 seconds. At the same time, the ICP alarm information is presented in the unit for details of a patient state (that is, the second alarm area). This parameter information is associated with an abnormal state of brain of the patient. Therefore, by combining this information with the human body diagram, a brain abnormality of the patient can be reflected. Wherein the time information expresses that the physiological parameter signal exceeds its safety threshold for a time period (i.e. the duration of the alarm). In other examples, the unit for details of a patient state can also combine sound, light, and other indication information to further remind the current alarm information.

Furthermore, in other examples, at least one item of alarm information, which is associated with the patient state and presented in the combined alarm mode, can be presented via graph. For example, at least one item of alarm information, which is associated with the patient state and presented in the combined alarm mode, can be presented via a curve graph, a histogram, a bar graph, a box graph, a scatter graph, a broken line graph, or a combination thereof, so that medical staff can more intuitively understand changes in the physiological parameter itself and/or changes in the comparison result of the physiological parameter with the preset alarm condition.

In an embodiment of this disclosure, the processor 120 may also control the display 130 to present a trend graph of at least one physiological parameter signal in a preset time period, wherein the trend graph is configured to reflect an evolution situation of the at least one physiological parameter signal in the preset time period. For example, the patient state window 420 further includes a display unit for a change of physical sign that presents a trend graph in a preset time period for at least one physiological parameter signal (such as the physiological parameter signal presented in the unit for details of a patient state 4202 or other physiological parameter(s)). This trend graph is configured to reflect an evolution situation of the physiological parameter in the preset time period, which allows medical staff to have a more detailed understanding of the evolution situation of the physiological parameter, which is associated with the current patient state. The trend graph of the physiological parameter may include a trend graph of a parameter value of the physiological parameter (for example, a heart rate value), or may include trend graphs of some abnormal events, which correspond to the physiological parameter (for example, an arrhythmia event corresponding to the electrocardiogram parameter, such as atrial fibrillation, ventricular fibrillation, etc.). In the example shown in FIG. 4, the display unit for a change of physical sign shows a fluctuation of HR and waveforms of blood oxygen saturation (SpO2), which are associated with the information of the physiological parameters displayed in the unit for details of a patient state.

Figure 6:
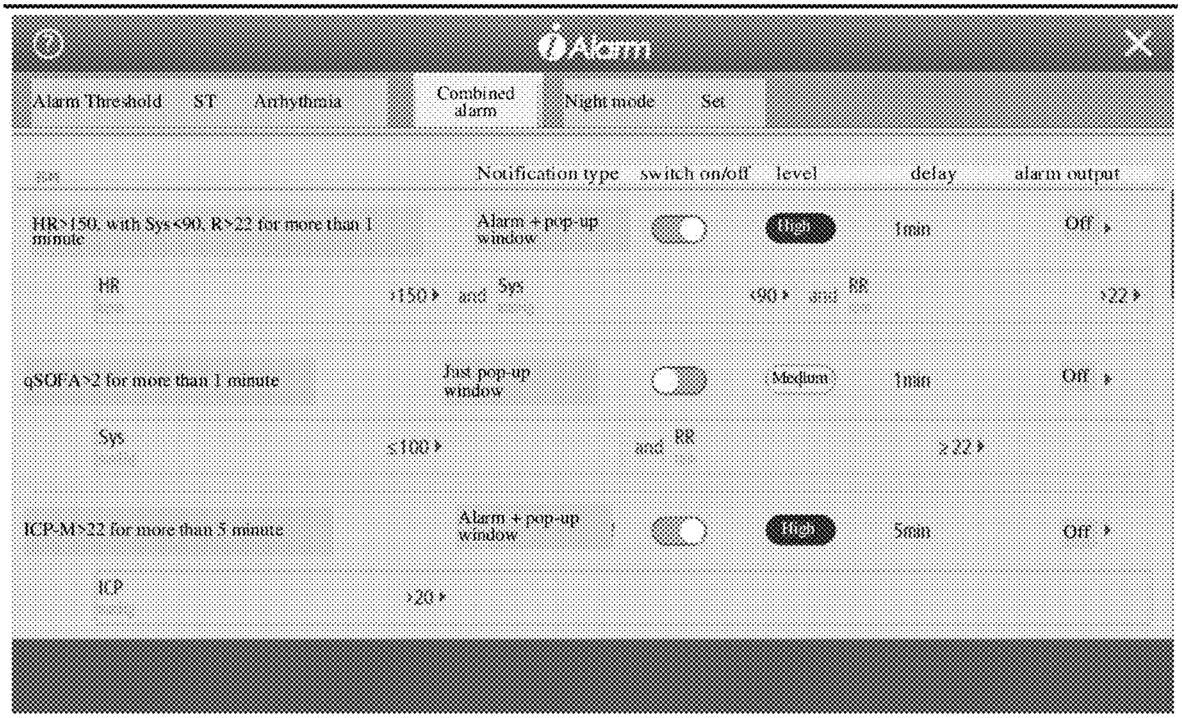
FIG. 6 is a diagram for an alarm setting interface of an embodiment in a patient monitoring device provided by this disclosure.

In order to facilitate the setting of upgraded alarm which is presented in the combined alarm mode, so that the user can adjust as needed one or more of the combined alarms that need to be alarmed, FIG. 6 shows a schematic diagram of an alarm setting interface of an embodiment of a patient monitoring device provided by this disclosure. The alarm setting interface includes a tab for setting a combined alarm, which tab is provided with multiple controls, such as a control for switching an alarm, a control for a type of alarm notification, a control for an alarm threshold, and a control for outputting an alarm. The first alarm rule and the second alarm rule are associated and set through the alarm setting interface. Specifically, the alarm setting interface includes a setting interface for combined alarm, which is configured to display a first alarm setting and a second alarm setting in an associated combination mode, wherein the first alarm setting is configured to generate or display the first alarm rule, and the second alarm setting is configured to generate or display the second alarm rule.

Optionally, the first alarm rule includes an alarm rule for exceeding a threshold and/or an alarm rule for an abnormal event, which alarm rule(s) is(are) associated with a first physiological parameter in the at least one physiological parameter signal; the second alarm rule includes an alarm rule for exceeding a threshold and/or an alarm rule for an abnormal event, which alarm rule(s) is(are) associated with a second physiological parameter, wherein the second physiological parameter is different from the first physiological parameter.

In order to facilitate the user to adaptively adjust the alarm rule for the combined alarm, when at least one of the first alarm rule and the second alarm rule includes an alarm rule for exceeding a threshold, the processor is further configured to adjust an alarm threshold of the alarm rule for exceeding a threshold, when receiving an instruction for adjusting the alarm threshold. For example, the instruction for adjusting the alarm threshold can be inputted by operating the control for an alarm threshold, so as to adjust the alarm threshold of the alarm rule for exceeding a threshold to a threshold which is instructed by said instruction.

In some embodiments, as shown in FIG. 6, the tab for setting a combined alarm may also include a variety of options for a combined alarm, wherein each option for a combined alarm may be an associated combination of one or more alarm rules, and each option for a combined alarm can enable or disable a corresponding combined alarm through the control for switching an alarm. For example, the processor 20 can be configured to, in response to an instruction for operating the control for switching an alarm, enable or disable a corresponding option for a combined alarm. The processor is configured to analyse a physiological parameter signal, which is associated with a combination alarm, that alarm is represented by an option for a combined alarm in a turned-on state. When a corresponding combination alarm is generated, the processor 20 can be further configured to at least store the combined alarm for easy review. When the control for outputting an alarm is turned on, the combined alarm is outputted in real-time, and when the control for outputting an alarm is turned off, the combined alarm is not outputted in real-time.

In some embodiments, as shown in FIG. 6, the tab for setting a combined alarm may also include a delay setting option, which is configured to indicate or set the first alarm information to be presented in the second presentation mode, when the physiological parameter signal simultaneously satisfies the first alarm rule and the second alarm rule, and a duration exceeds a first preset time length, in which duration the physiological parameter signal simultaneously satisfies the first alarm rule and the second alarm rule; or to indicate or set the first alarm information to be presented in the second presentation mode, when the physiological parameter signal satisfies the first alarm rule, and a duration exceeds a second preset time length, in which duration the physiological parameter signal satisfies the first alarm rule. The delay setting option can be used to set the time-related preset time length in each option of a combined alarm. For example, when an instruction for adjusting a time length is inputted through the delay setting option, the processor is further configured to adjust the first preset time length or the second preset time length to said time length which is instructed by said instruction, so that the user can flexibly adjust the preset time length according to actual needs through the delay setting option.

Figure 7:
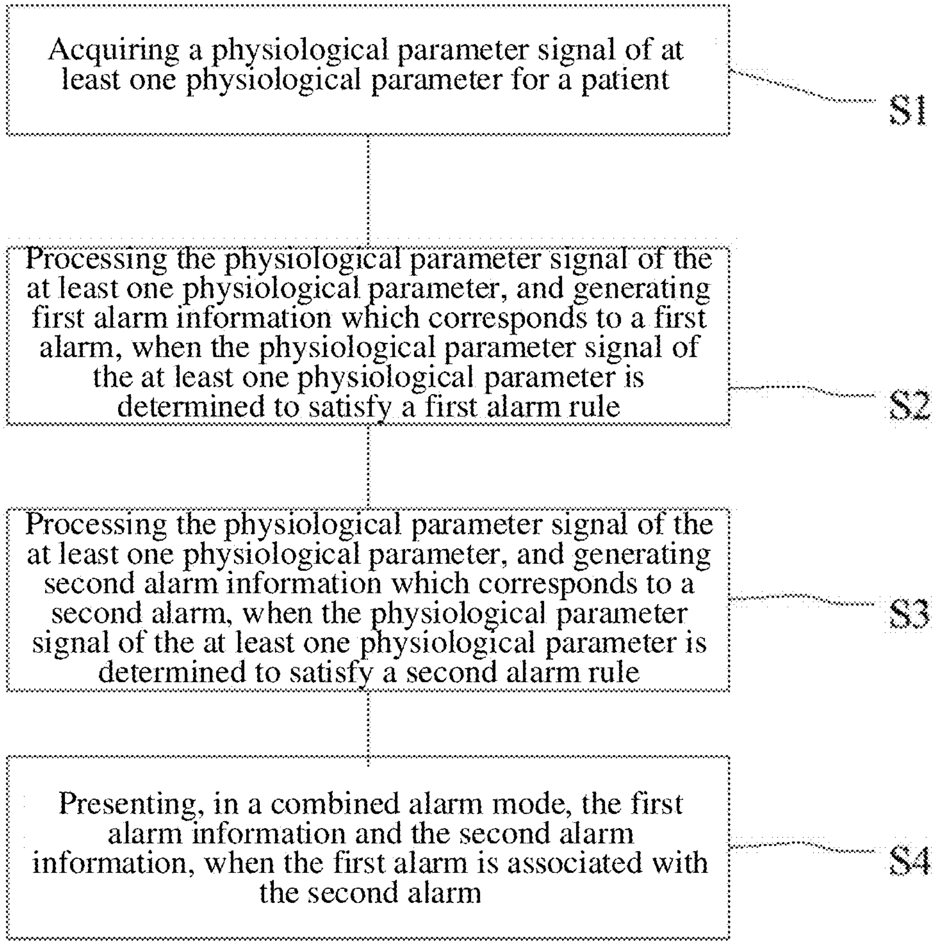
FIG. 7 is a flow chart of an embodiment of an alarm method for patient monitoring provided by this disclosure.

Please refer to FIG. 7, which shows a flow chart of an embodiment of an alarm method for patient monitoring, including:

S1. acquiring a physiological parameter signal of at least one physiological parameter for a patient;

S2. processing the physiological parameter signal of the at least one physiological parameter, and generating first alarm information which corresponds to a first alarm, when the physiological parameter signal of the at least one physiological parameter is determined to satisfy a first alarm rule;

S3. processing the physiological parameter signal of the at least one physiological parameter, and generating second alarm information which corresponds to a second alarm, when the physiological parameter signal of the at least one physiological parameter is determined to satisfy a second alarm rule;

S4. presenting, in a combined alarm mode, the first alarm information and the second alarm information, when the first alarm is associated with the second alarm.

In one embodiment, the combined alarm mode includes adding an associated character string to the first alarm information and the second alarm information, so as to form single piece of combined alarm information for presentation, wherein the associated character string represents that the second alarm accompanies with the first alarm.

In one embodiment, the first alarm information is presented at a first alarm level, and the single piece of combined alarm information is presented at a second alarm level, wherein the second alarm level is higher than the first alarm level.

In one embodiment, the combined alarm mode includes adding an associated character string to the first alarm information and the second alarm information, so as to form single piece of combined alarm information for presentation, wherein the associated character string represents that the second alarm accompanies with the first alarm. For example, the first alarm information is presented at a first alarm level, and the single piece of combined alarm information is presented at a second alarm level, wherein the second alarm level is higher than the first alarm level.

The alarm method for patient monitoring of this disclosure can be implemented by the aforementioned patient monitoring device, some details of this embodiment can be referred to the previous description and will not be repeated here.

Through the method of this disclosure, the alarm presentation mode is upgraded by a combined alarm, so that the alarm is relatively more likely to attract the attention of medical staff, thereby reminding medical staff in a more eye-catching manner that the alarm causes an increased pathological risk due to the simultaneous existence of an associated second alarm, thereby attracting the attention of medical staff in a timely manner and achieving more timely patient intervention.

One skilled in the art can understand that all or part of the processes in the above-mentioned embodiment methods can be implemented by instructing related hardware through a computer program. The computer program can be stored in a computer-readable storage medium. When the program is executed, it can include the processes of the embodiments of the above-mentioned methods. The aforementioned storage medium may be a non-volatile storage medium such as a magnetic disk, an optical disk, a read-only memory (ROM), or a random-access memory (RAM).

It should be understood that, although the steps in the flowchart of the accompanying drawings are displayed sequentially as indicated by the arrows, these steps are not necessarily executed sequentially in the order indicated by the arrows. Unless otherwise specified herein, there is no strict order limitation for the execution of these steps, and they may be executed in other orders. Moreover, at least part of the steps in the flowchart of the accompanying drawings may include multiple sub-steps or multiple stages. These sub-steps or stages are not necessarily executed at the same time, but can be executed at different times. The order of execution is not necessarily sequential, but can be executed in turn or alternately with other steps or at least part of the sub-steps or stages of other steps.

This disclosure has been described with reference to various exemplary embodiments. However, those skilled in the art recognizes that changes and modifications may be made to the exemplary embodiments without departing from the scope of the disclosure. For example, the various operational steps and components for performing the operational steps may be implemented in different ways (e.g., one or more steps may be deleted, modified, or combined into other steps), depending on the specific application or considering any number of cost functions associated with the operation of the system.

Additionally, as appreciated by those skilled in the art, the principles of this document may be reflected in a computer program product on a computer-readable storage medium pre-installed with computer-readable program code. Any tangible, non-transitory computer-readable storage medium may be used, including magnetic storage devices (hard disks, floppy disks, etc.), optical storage devices (CD-ROMs, DVDs, Blu Ray disks, etc.), flash memory, and/or the like. These computer program instructions may be loaded onto a general-purpose computer, a special-purpose computer, or other programmable data processing apparatus to form a machine, so that these instructions executed on the computer or other programmable data processing apparatus may generate means for implementing the specified functions. These computer program instructions may also be stored in a computer-readable memory, which may instruct a computer or other programmable data processing apparatus to operate in a specific manner, such that the instructions stored in the computer-readable memory may form an article of manufacture, including an implementation device that implements the specified functions. Computer program instructions may also be loaded onto a computer or other programmable data processing apparatus so that a series of operational steps are performed on the computer or other programmable device to produce a computer-implemented process, so that the instructions executed on the computer or other programmable device may provide steps for implementing specified functions.

Although the principles herein have been illustrated in various embodiments, many modifications of structure, arrangement, proportions, elements, materials, and components specifically adapted to particular environments and operating requirements may be used without departing from the principles and scope of this disclosure. The above modifications and other changes or corrections are intended to be included within the scope of this document.

The foregoing detailed description has been described with reference to various embodiments. However, one skilled in the art appreciates that various modifications and changes can be made without departing from the scope of this disclosure. Accordingly, this disclosure is to be considered in an illustrative rather than a restrictive sense, and all such modifications are intended to be included within the scope thereof. Likewise, advantages, other advantages, and solutions to problems have been described above with regard to various embodiments. However, benefits, advantages, solutions to problems, and any elements that produce the same, or render them more evident, should not be explained as critical, required, or essential. As used herein, the term “include” and any other variations thereof are intended to be non-exclusive inclusions, such that a process, method, article, or apparatus that includes a list of elements, includes not only those elements but also other elements that are not expressly listed or that do not belong to the process, method, system, article, or apparatus. Furthermore, the term "coupled connection", and any other variations thereof as used herein refers to a physical, electrical, magnetic, optical, communicative, functional, and/or any other connection.

Those skilled in the art appreciate that many changes may be made to the details of the above-described embodiments without departing from the underlying principles of this disclosure. Accordingly, the scope of this disclosure should be determined from the following claims.

What is claimed is:

1. A patient monitoring device, comprising:

a signal acquiring apparatus, which is configured to acquire a physiological parameter signal of at least one physiological parameter for a patient;

a processor, which is configured to process the physiological parameter signal of the at least one physiological parameter, and generate a first alarm when determining that the physiological parameter signal of the at least one physiological parameter satisfies a first alarm rule; and a display, which is configured to display, in a first alarm area, first alarm information in a first presentation mode, wherein the first alarm information represents the first alarm;

wherein the processor is further configured to determine whether the physiological parameter signal of the at least one physiological parameter simultaneously satisfies a second alarm rule and the first alarm rule, and control the display to simultaneously display the first alarm information and second alarm information in a second presentation mode when determining that the physiological parameter signal of the at least one physiological parameter simultaneously satisfies the first alarm rule and the second alarm rule; wherein the second alarm rule is different from the first alarm rule, and the second presentation mode is an upgrade based on the first presentation mode and indicates that physiological state of the patient is more serious in the second presentation mode than the first presentation mode.

2. The patient monitoring device according to claim 1, wherein, the first presentation mode comprises displaying the first alarm information in the first alarm area with a first background color; and the second presentation mode comprises one mode of:

displaying the first alarm information in the first alarm area with a second background color, wherein the second background color has a stronger warning effect than the first background color;

enlarging the first alarm area, and displaying the first alarm information in the enlarged first alarm area;

displaying the first alarm information in the first alarm area with the first background color or the second background color, wherein the first background color or the second background color is flashed; and displaying the first alarm information in a second alarm area which is outside the first alarm area.

3. The patient monitoring device according to claim 1, wherein, the second presentation mode comprises simultaneously displaying the second alarm information and the first alarm information in an associated combination mode;

wherein the second alarm information represents that the physiological parameter signal of the at least one physiological parameter satisfies the second alarm rule.

4. The patient monitoring device according to claim 3, wherein, the second alarm information is in associated combination with the first alarm information through an associated character string;

wherein the associated character string comprises text, symbol(s), and/or mark(s).

5. The patient monitoring device according to claim 3, wherein, the second alarm information and the first alarm information are simultaneously displayed in the associated combination mode in a second alarm area, wherein the second alarm area is independent from the first alarm area;

wherein the first alarm area and the second alarm area are arranged side by side, from up to down or from left to right;

wherein a background color of the first alarm area has a stronger warning effect than a background color of the second alarm area; or the second alarm information and the first alarm information are simultaneously displayed in the associated combination mode in the first alarm area.

6. The patient monitoring device according to claim 1, further comprising an audio outputting apparatus, wherein the second presentation mode comprises: adding or enhancing, through the audio outputting apparatus, an alarm sound along with a presentation of the first alarm information.

7. The patient monitoring device according to claim 1, wherein, the at least one physiological parameter comprises a first physiological parameter, and the physiological parameter signal comprises a first physiological parameter signal; wherein the first alarm rule and the second alarm rule are both associated with the first physiological parameter.

8. The patient monitoring device according to claim 7, wherein, the first alarm rule is an alarm rule for exceeding a threshold or an alarm rule for an event, which is associated with the first physiological parameter; and the second alarm rule is that a duration of an alarm exceeds a preset time length, when the alarm satisfies the first alarm rule.

9. The patient monitoring device according to claim 8, wherein, the first physiological parameter comprises a blood oxygen saturation parameter, an electrocardiogram parameter, a respiratory parameter, or a blood pressure parameter; and the first alarm rule comprises that the first physiological parameter signal exceeds an alarm threshold.

10. The patient monitoring device according to claim 1, wherein, the at least one physiological parameter comprises a first physiological parameter and a second physiological parameter that is different from the first physiological parameter; the physiological parameter signal comprises a first physiological parameter signal and a second physiological parameter signal; and the first alarm rule is associated with the first physiological parameter, and the second alarm rule is associated with the second physiological parameter.

11. The patient monitoring device according to claim 10, wherein, the first physiological parameter is a blood oxygen saturation parameter; and the first alarm comprises an alarm for extremely-low SpO2, an alarm for too-low SpO2, an alarm for extremely-low SpO2b, or an alarm for too-low SpO2b; and the second physiological parameter is a respiratory parameter, and the second alarm rule is that a signal of said respiratory parameter satisfies a threshold for too-high respiratory rate, or a threshold for too-low respiratory rate.

12. The patient monitoring device according to claim 10, wherein, the first physiological parameter is a blood pressure parameter, and the first alarm rule comprises an alarm rule for too-low arterial pressure; and the second physiological parameter is an electrocardiogram parameter; and the second alarm rule comprises at least one of: an alarm rule for too-low HR, an alarm rule for bradycardia, an alarm rule for tachycardia, an alarm rule for atrial fibrillation, an alarm rule for ventricular rhythm, an alarm rule for bigeminy ventricular premature contraction, an alarm rule for trigeminy premature ventricular contraction, an alarm rule for too-high ST, an alarm rule for too-low ST, an alarm rule for a single ΔST that exceeds a threshold, and an alarm rule for multiple ΔSTs that exceed threshold(s).

13. The patient monitoring device according to claim 10, wherein, the processor is further configured to control the display to simultaneously present the first alarm information and the second alarm information in an associated combination mode, when determining that the first physiological parameter satisfies the first alarm rule, and the second physiological parameter satisfies the second alarm rule;

the second alarm rule comprises: the second physiological parameter satisfies an alarm rule for exceeding a threshold and/or an alarm rule for an event; and duration(s) exceed(s) preset time length(s), in which duration(s) the second physiological parameter satisfies the alarm rule for exceeding a threshold and/or the alarm rule for an event; and the first alarm information represents that the first physiological parameter satisfies the first alarm rule, and the second alarm information represents that the second physiological parameter satisfies the second alarm rule.

14. The patient monitoring device according to claim 1, wherein, the display further comprises an alarm setting interface, wherein the first alarm rule and the second alarm rule are set through the alarm setting interface;

wherein the alarm setting interface comprises a setting interface for combined alarm, wherein the setting interface for combined alarm is configured to display a first alarm setting and a second alarm setting in an associated combination mode, wherein the first alarm setting is configured to generate or display the first alarm rule, and the second alarm setting is configured to generate or display the second alarm rule.

15. The patient monitoring device according to claim 14, wherein, the first alarm rule comprises: an alarm rule for exceeding a threshold and/or an alarm rule for an event, which alarm rule(s) is (are) associated with a first physiological parameter; and the second alarm rule comprises: an alarm rule for exceeding a threshold and/or an alarm rule for an event, which alarm rule(s) is (are) associated with a second physiological parameter, wherein the second physiological parameter is different from the first physiological parameter.

16. The patient monitoring device according to claim 14, wherein, when at least one of the first alarm rule and the second alarm rule comprises an alarm rule for exceeding a threshold, the processor is further configured to, when receiving an instruction for adjusting a threshold, which instruction is for an alarm threshold of said alarm rule for exceeding a threshold, adjust the alarm threshold of said alarm rule for exceeding a threshold, to a threshold which is instructed by said instruction.

17. The patient monitoring device according to claim 14, wherein, the setting interface for combined alarm further comprises a delay setting option;

wherein the delay setting option is configured to indicate or set the first alarm information to be presented in the second presentation mode;

when the at least one physiological parameter signal simultaneously satisfies the first alarm rule and the second alarm rule, and a duration exceeds a first preset time length, in which duration the at least one physiological parameter signal simultaneously satisfies the first alarm rule and the second alarm rule; or the delay setting option is configured to indicate or set the first alarm information to be presented in the second presentation mode, when the at least one physiological parameter signal satisfies the first alarm rule, and a duration exceeds a second preset time length, in which duration the at least one physiological parameter signal satisfies the first alarm rule.

18. The patient monitoring device according to claim 17, wherein, when an instruction for adjusting a time length is inputted through the delay setting option, the processor is further configured to adjust the first preset time length or the second preset time length to a time length which is instructed by said instruction.

19. A patient monitoring device, comprising:

a signal acquiring apparatus, which is configured to acquire a physiological parameter signal of at least one physiological parameter for a patient;

a processor, which is configured to generate a first alarm when the physiological parameter signal of the at least one physiological parameter satisfies a first alarm rule, and generate a second alarm when the physiological parameter signal of the at least one physiological parameter satisfies a second alarm rule; and a display, which is configured to display first alarm information and second alarm information, wherein the first alarm information represents the first alarm and is configured to be displayed in a first presentation mode, and the second alarm information represents the second alarm;

wherein the display is further configured to output, in a combined alarm mode, the first alarm information and the second alarm information configured to be simultaneously displayed in a second presentation mode, when the physiological parameter signal of the at least one physiological parameter simultaneously satisfies the first alarm rule and the second alarm rule, wherein the second presentation mode is an upgrade based on the first presentation mode and indicates that physiological state of the patient is more serious in the second presentation mode than the first presentation mode.

20. An alarm method for patient monitoring, comprising:

acquiring a physiological parameter signal of at least one physiological parameter for a patient;

processing the physiological parameter signal of the at least one physiological parameter, and generating first alarm information which corresponds to a first alarm and is configured to be displayed in a first presentation mode, when the physiological parameter signal of the at least one physiological parameter is determined to satisfy a first alarm rule;

processing the physiological parameter signal of the at least one physiological parameter, and generating second alarm information which corresponds to a second alarm, when the physiological parameter signal of the at least one physiological parameter is determined to satisfy a second alarm rule; and presenting, in a combined alarm mode, the first alarm information and the second alarm information configured to be simultaneously displayed in a second presentation mode, when the first alarm is associated with the second alarm and the physiological parameter signal of the at least one physiological parameter simultaneously satisfies the first alarm rule and the second alarm rule, wherein the second presentation mode is an upgrade based on the first presentation mode and indicates that physiological state of the patient is more serious in the second presentation mode than the first presentation mode.

* * * * *